United States Patent
Anderson et al.

(10) Patent No.: US 9,366,613 B2
(45) Date of Patent: Jun. 14, 2016

(54) MATRIX PERMITIVITY DETERMINATION

(75) Inventors: Valerie Anderson, Hardwick (GB);
Gerald Meeten, Ware (GB); Andrew Clarke, Haslingfield (GB); Tianhua Zhang, Chatillon (FR); Patrice Ligneul, Chaville (FR)

(73) Assignee: SCHLUMBERGER TECHNOLOGY CORPORATION, Sugar Land, TX (US)

(*) Notice: Subject to any disclaimer, the term of this patent is extended or adjusted under 35 U.S.C. 154(b) by 263 days.

(21) Appl. No.: 14/126,413

(22) PCT Filed: Jun. 20, 2012

(86) PCT No.: PCT/IB2012/053105
§ 371 (c)(1),
(2), (4) Date: Feb. 17, 2014

(87) PCT Pub. No.: WO2012/176129
PCT Pub. Date: Dec. 27, 2012

(65) Prior Publication Data
US 2014/0184230 A1 Jul. 3, 2014

(30) Foreign Application Priority Data
Jun. 23, 2011 (GB) .................... 1110665.5

(51) Int. Cl.
*G01N 15/08* (2006.01)
*G01N 33/24* (2006.01)
*E21B 49/00* (2006.01)

(52) U.S. Cl.
CPC ............. *G01N 15/08* (2013.01); *E21B 49/00* (2013.01); *G01N 15/088* (2013.01); *G01N 33/24* (2013.01)

(58) Field of Classification Search
CPC ............................. G01N 27/221; G01N 33/24
See application file for complete search history.

(56) References Cited

U.S. PATENT DOCUMENTS

| | | | |
|---|---|---|---|
| 4,996,489 A | 2/1991 | Sinclair | |
| 5,073,756 A | 12/1991 | Brandelik | |
| 5,898,310 A | 4/1999 | Liu | |
| 7,199,591 B2 | 4/2007 | Katsufumi | |
| 2003/0008129 A1 | 1/2003 | Cotte et al. | |
| 2005/0264302 A1 | 12/2005 | Mohajer et al. | |
| 2009/0261847 A1 | 10/2009 | Petrovsky et al. | |
| 2011/0138928 A1 | 6/2011 | Xie et al. | |
| 2012/0153958 A1* | 6/2012 | Anderson | G01V 3/30 324/332 |

(Continued)

FOREIGN PATENT DOCUMENTS

| | | |
|---|---|---|
| EP | 1528618 | 5/2005 |
| JP | 08075630 | 3/1996 |
| JP | 2008075630 A | 4/2008 |

OTHER PUBLICATIONS

Anderson et al., "Permittivy Measurement of Minerals," IoP Dielectrics Group Meeting: University of Kent, Apr. 2011: p. 1.

(Continued)

*Primary Examiner* — Tung X Nguyen
*Assistant Examiner* — Feba Pothen

(57) ABSTRACT

A method and system for determining a rock matrix dielectric permittivity. The method and system use a matching liquid with a temperature dependant permittivity. The matching liquid may be used in an automated and/or downhole system for measuring matrix dielectric permittivity of rock formations.

19 Claims, 8 Drawing Sheets

(56) References Cited

U.S. PATENT DOCUMENTS

2012/0273273 A1* 11/2012 Ligneul ............... G01N 27/221 175/46
2012/0293180 A1* 11/2012 Chae ................... G01N 27/221 324/347

OTHER PUBLICATIONS

Anderson et al., "Permittivity measurements of minerals," Journal of Physics: Conference Series, 2013, vol. 472: pp. 1-5.

Kaye & Laby, "2.6.5: Dielectric properties of materials," General Physics, Electricity and magnetism, 1995: pp. 1-8, <http://www.kayelaby.npl.co.uk/general_physics/2_6/2_6_5.html>.

International Search Report of PCT Application No. PCT/IB2012/053105 dated Jan. 31, 2013: pp. 1-2.

Combined Search and Examination Report of British Application No. GB1110665.5 dated Oct. 4, 2011: pp. 1-6.

Jylha et al., "Equation for the effective permittivity of particle-filled composites for material design applications," J. Phys. D: Appl. Phys., 2007, vol. 40: pp. 4966-4973.

Examination Report issued in GC2012-21405 on Dec. 31, 2014, 4 pages.

* cited by examiner

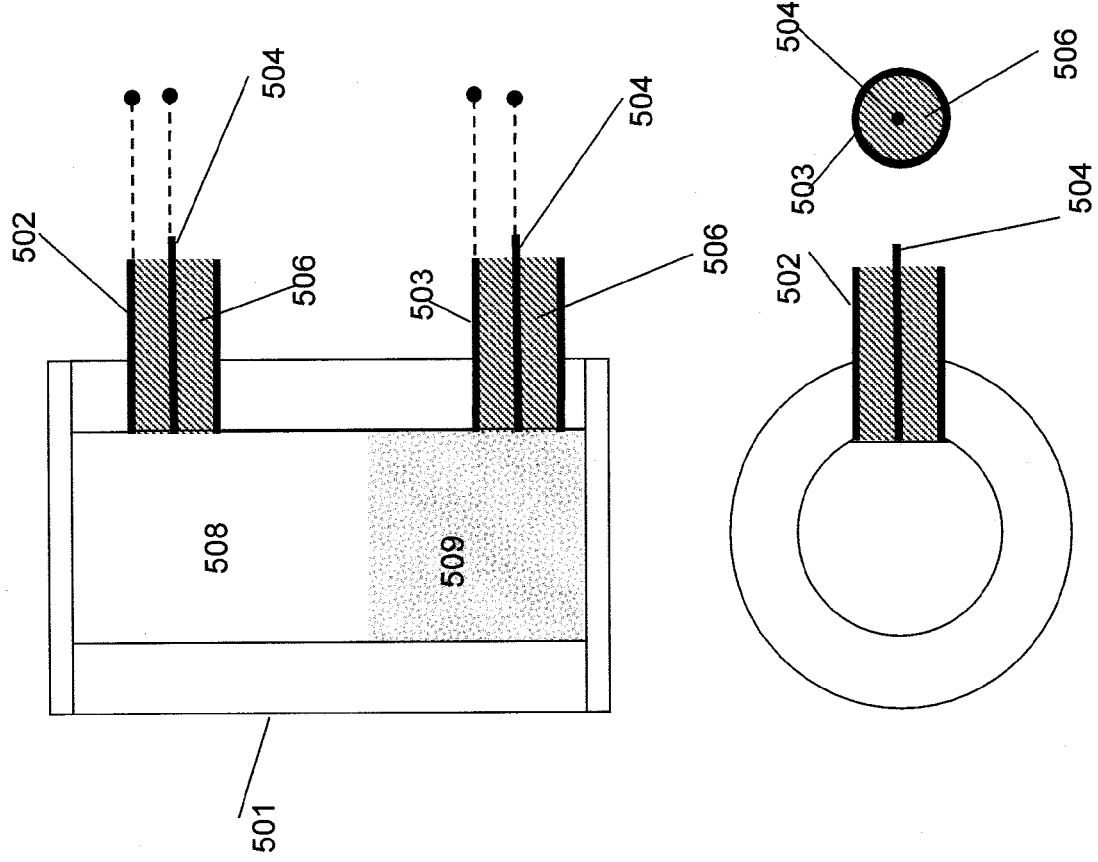

TE$_{01\delta}$ Cavity coupling

MATRIX PERMITIVITY DETERMINATION

CROSS-REFERENCE TO RELATED APPLICATIONS

This application is a U.S. National Stage Application under 35 U.S.C. §371 and claims priority to Patent Cooperation Treaty Application No. PCT/IB2012/053105 filed Jun. 20, 2012, which claims priority to British Patent Application No. GB1110665.5 filed Jun. 23, 2011. Both of these applications are incorporated herein by reference in their entireties.

BACKGROUND OF THE DISCLOSURE

To understand earth formations and how such formations behave, it is necessary to determine the permittivity of the rock comprising the formation. For example, in order to produce hydrocarbons economically, a reasonably accurate estimation of hydrocarbon volume and mobility needs to be performed. The measurement of dielectric constant (or dielectric permittivity) of formations surrounding a borehole is known to provide useful information about the formations for hydrocarbon transport purposes. The dielectric constant of the different materials in earth formations vary widely—for example, dielectric constants are roughly 2.2 for oil, 7.5 for limestone, and 80 for water—so measurement of dielectric properties can be a useful means of formation evaluation.

For hydrocarbon production purposes, effective measurement of formation permittivity and/or conductivity must be performed. The earth formation consists of the rock matrix and the pore fluids—usually hydrocarbon and water—that are present in and/or may pass through the pores in the rock matrix. In order to deduce the volumetric fraction of water in the formation from the effective permittivity of the formation, a relationship between the properties of the constituents of the formation and the mixture of the constituents (known as a "mixing rule") is generally used. Among several existing dielectric mixing rules, the Complex Refractive Index Method ("CRIM") is one of the most widely used. A disadvantage of mixing rules is that they require knowledge of both the matrix and fluid complex permittivity, which knowledge may be difficult to ascertain.

For purposes of this application, a rock will be regarded as including a porous and permeable solid mineral matrix, comprising for example sandstone or carbonate grains. Previously, the permittivity of such a rock has been measured when saturated with a fluid that occupies the pores of the rock. However, obtaining solely the rock matrix permittivity—often termed the "dry rock permittivity"—from such measurements on saturated rock is problematic because of the contribution of the pore space in the rock to the rock matrix permittivity; which contribution cannot be determined from the saturated rock measurement. A similar problem applies to obtaining the permittivity of the rock matrix from permittivity measurements made on a powdered sample of the rock, e.g. in a measurement system where the grains of the powdered rock sample are suspended in a liquid or gaseous dielectric; the problem arising again from the fact that the permittivity effects of the pore space in the rock matrix cannot be measured from the saturated powder as the fluid saturating the pores mixes the effect of the pores with the measured permittivity.

As discussed above, calculating the permittivity of a rock core or a powder sampled from a formation requires the use of mixture rules that relate the permittivity of a mixture of rock and liquid in a sample to the individual permittivities of the solid and the liquid components of the sample. Mixture rules use the permittivities of the components of the mixture and the volume fraction of each of the components in the mixture as parameters. However, the mixture rules are of unknown validity and can differ markedly from one another, and hence can produce large errors in rock matrix permittivity values that are derived from saturated rock permittivity measurements.

BRIEF SUMMARY OF THE DISCLOSURE

In one embodiment of the present invention, a matching liquid is used to saturate a porous rock sample. The matching liquid may for example have a permittivity that is dependent on temperature. In accordance with an embodiment of the present invention, the permittivity of the porous sample may be determined by saturating the rock sample in the matching liquid, measuring the permittivity of the sample as a function of temperature, and determining the temperature and hence the liquid permittivity that matches the permittivity of the porous sample.

In certain embodiments of the present invention, a dielectric permittivity of a porous material may be determined by measuring a first indicator indicative of a first dielectric permittivity of a fluid composition, which composition may comprise a single component or a mixture of components. The fluid composition has a dielectric permittivity that changes with a thermodynamic property of the composition, such as temperature. The porous material is saturated with the fluid composition and a first response indicative of the dielectric permittivity of the saturated porous material is measured. The thermodynamic property of the fluid mixture is then altered and a second indicator indicative of a second dielectric permittivity of the fluid composition under the altered thermodynamic property is measured. The first and the second indicators may be used to process the dielectric permittivity of the porous material.

Further measurements indicative of the dielectric permittivity of the saturated porous material at under different thermodynamic conditions may be made to process the matrix permittivity. The processing may include using differential measurements. The measurements indicative of the dielectric permittivity of the saturated porous material may be processed to determine the extent of changes to be made to the thermodynamic properties of the saturated porous material. For example, the thermodynamic properties of the composition, the measurements indicative of the dielectric permittivity of the saturated porous material may be processed and the measurements indicative of the dielectric permittivity of the composition may be processed in real time to ensure that the thermodynamic properties are adjusted such that the dielectric permittivity of the composition produced by the thermodynamic properties matches the dielectric permittivity of the porous material.

In other embodiments of the present invention, a porous material is saturated in a fluid composition that has a dielectric permittivity that changes with the thermodynamic property of the composition. The saturated composition is disposed in a container so that a portion of the fluid composition, a reservoir of the fluid composition that is not saturating the porous material, can be analyzed separately/independently from the saturated porous material. Merely by way of example, the saturated porous material may be immersed in, partially immersed in and/or in contact with a reservoir of the fluid composition. In such a configuration, probes may be used to determine properties of the saturated porous material and the reservoir of the fluid composition. Alternatively, by changing the orientation of the container, the relative amount of the fluid composition and the saturated porous material being investigated by a probe or the like may be varies.

In other aspects, a reservoir of the fluid composition may be kept in a separate container to the porous material so that properties of the saturated porous material and the reservoir of the fluid composition may be determined separately/independently. In other aspects, the reservoir of the fluid composition may be kept in a separate container to the porous material to provide for independent analysis of the reservoir of the fluid composition and the porous material and the two containers may be in fluid communication. A device, such as a heater or the like, may be used to change the thermodynamic property of the reservoir and the saturated porous material. A first permittivity measuring device may be used to measure responses indicative of the permittivity of the reservoir and a second permittivity measuring device may be used to measure responses indicative of the permittivity of the saturated porous material.

The permittivity measuring devices may comprise antennas for measuring responses indicative of the capacitance of the reservoir and/or the saturated porous material. The permittivity measuring devices may comprise a resonator cavity for making resonator measurements indicative of the permittivity of the reservoir and/or the saturated porous material.

In an aspect of the present invention, a processor is configured to process the dielectric permittivity of the porous material from measurements from the first permittivity measuring device and the second permittivity measuring device, wherein the processor processes at least two measurements from the first and the second permittivity measuring device made at at least two different thermodynamic properties.

BRIEF DESCRIPTION OF THE DRAWINGS

The present disclosure is described in conjunction with the appended figures:

FIGS. 5A and 5B illustrate a system using high frequency interrogation for determining a rock matrix permittivity of a powdered rock sample, in accordance with an embodiment of the present invention;

Figure 1:
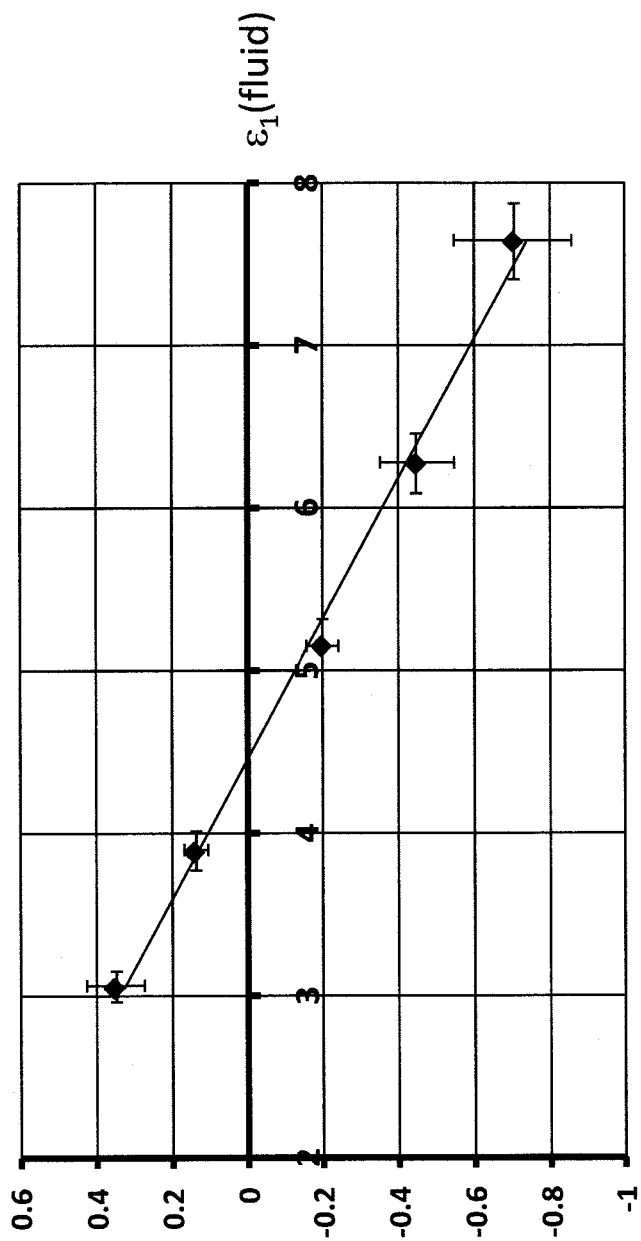
FIG. 1 shows the dependence of the difference between the permittivity of a mixture of a sample of the rock matrix saturated in a matching liquid $\in_1$ (combined permittivity $\in$) and the permittivity of the matching liquid $\in_1$ on the permittivity of the matching liquid $\in_1$, for use in an embodiment of the present invention.

In the appended figures, similar components and/or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION

The ensuing description provides preferred exemplary embodiment(s) only, and is not intended to limit the scope, applicability or configuration of the invention. Rather, the ensuing description of the preferred exemplary embodiment(s) will provide those skilled in the art with an enabling description for implementing a preferred exemplary embodiment of the invention. It being understood that various changes may be made in the function and arrangement of elements without departing from the scope of the invention as set forth in the appended claims.

Specific details are given in the following description to provide a thorough understanding of the embodiments. However, it will be understood by one of ordinary skill in the art that the embodiments maybe practiced without these specific details. For example, circuits may be shown in block diagrams in order not to obscure the embodiments in unnecessary detail. In other instances, well-known circuits, processes, algorithms, structures, and techniques may be shown without unnecessary detail in order to avoid obscuring the embodiments.

Also, it is noted that the embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed, but could have additional steps not included in the figure. A process may correspond to a method, a function, a procedure, a subroutine, a subprogram, etc. When a process corresponds to a function, its termination corresponds to a return of the function to the calling function or the main function.

Moreover, as disclosed herein, the term "storage medium" may represent one or more devices for storing data, including read only memory (ROM), random access memory (RAM), magnetic RAM, core memory, magnetic disk storage mediums, optical storage mediums, flash memory devices and/or other machine readable mediums for storing information. The term "computer-readable medium" includes, but is not limited to, portable or fixed storage devices, optical storage devices, wireless channels and various other mediums capable of storing, containing or carrying instruction(s) and/or data.

Furthermore, embodiments may be implemented by hardware, software, firmware, middleware, microcode, hardware description languages, or any combination thereof. When implemented in software, firmware, middleware or microcode, the program code or code segments to perform the necessary tasks may be stored in a machine readable medium such as storage medium. A processor(s) may perform the necessary tasks. A code segment may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

In one embodiment, the present disclosure, among other aspects, provides a method that avoids the need of using a mixing rule and avoids the need to measure volume fraction to determine a rock matrix permittivity. In accordance with such an embodiment, the permittivity of the rock is measured in a matching liquid, i.e. a liquid with the same permittivity as the rock matrix. In such an arrangement, a rock sample saturated with a matching liquid will have the same permittivity as the liquid, and thus the liquid filled rock will behave in an electric field as a single homogeneous medium, thereby negating the necessity of a mixing rule or knowledge of porosity.

A permittivity matching liquid for a rock sample may be found by saturating the rock with a number of liquids of different and known permittivities. In the matching process, the rock is soaked with each of the liquids of known permittivity, the permittivity of the saturated rock is measured and the matching liquid is found by interpolation of the measurements.

In the permittivity matching method, fluids of controlled permittivity may be obtained by mixing two miscible liquids of different permittivity. For example, the matching method may be used to determine the permittivity of a calcium carbonate powder by suspending the powder in a fluid mixture of butan-1-ol and decane; where the fluid mixture permittivity can be varied by varying the liquid composition of the butan-1-ol and decane.

FIG. 1 shows the dependence of the difference between the permittivity of a mixture of a sample of the rock matrix saturated in a matching liquid $\in$ and the permittivity of the matching liquid $\in_1$ on the permittivity of the matching liquid $\in_1$, for use in an embodiment of the present invention. The rock sample in the depicted example is powdered silica. The matching liquid comprises a mixture of liquids and the amount of the liquids in the mixture to change the matching liquid permittivity $\in_1$. By changing the permittivity of the matching liquid $\in_1$ that the silica powder is suspended in and measuring the change in permittivity, the permittivity of the rock matrix $\in$ can be determined. For example, when the permittivity of the fluid mixture $\in$ is equal to the permittivity of the matching liquid $\in_1$, the difference between the two permittivities is zero and permittivity of the rock matrix is equal to the permittivity of the matching liquid. As provided in FIG. 1, when the difference between the permittivity of the mixture of a sample of the rock matrix saturated in a matching liquid 8 and the permittivity of the matching liquid $\in_1$ is zero, it can be found that permittivity of the rock matrix $\in_2$ is in the range of 4.43 to 4.63.

In the matching method, the permittivity of the fluid must be determined, the rock/powder must then be saturated by the fluid and this process must be repeated for fluids with different permittivities. Such a process may be time consuming and expensive. In one embodiment of the present invention, a thermodynamic parameter of a matching liquid is varied and this change in the thermodynamic parameter causes a change in the permittivity of the matching liquid. In this way, in a first step, a rock sample, rock core, rock powder may be saturated with the matching liquid at an initial temperature, a measurement indicative of the permittivity of the liquid may be recorded and a measurement indicative of the permittivity of the rock sample saturated by the liquid may also be measured.

In a second step of the embodiment of the present invention, a thermodynamic parameter may be changed. In certain aspects of the present invention, the thermodynamic parameter may comprise temperature and, as such, the temperature of the matching liquid may be changed. In a third step of the embodiment, a measurement indicative of the permittivity of the liquid at the changed temperature may be determined and a measurement indicative of the permittivity of the rock sample soaked in the liquid at the changed temperature may also be recorded. Merely by way of example, the second and third step may comprise heating the liquid to a certain temperature, heating the rock sample saturated in the liquid to the certain temperature and making the measurements indicative of permittivity of the matching liquid and the saturated rock sample at the certain temperature.

In some embodiments of the present invention, the permittivity indicative measurements taken at the initial and other certain temperatures may be used to calculate the rock matrix permittivity. In certain embodiments, measurements indicative of the permittivity of the matching liquid and the rock sample saturated with the liquid may be made at two temperatures and used to determine the rock matrix permittivity. In other embodiments, measurements indicative of the permittivity of the matching liquid and the rock sample saturated with the liquid may be made at three or more different temperatures may be measured and used to determine the permittivity of the rock matrix.

In the case of a rock of permittivity $\in_2$ a matching liquid may be used to saturate the rock matrix. In the case of a powder whose grains permittivity is $\in_2$, a matching liquid may either suspend and/or permeate the suspended or sedimented powder, and is regarded as saturating the powder. The permittivity of the saturated rock or the powder suspension is denoted by $\in$ and the permittivity of the matching liquid is denoted by $\in_1$, such that in the case of a perfect match between the matching liquid and the solid phase permittivity of the rock sample:

$$\in = \in_1 = \in_2 \qquad (1)$$

In the case of an imperfect match where $\in_1 \neq \in_2$, a Taylor expansion of $\in$ around $\in_2$ provides:

$$\varepsilon = \varepsilon_2 + \sum_{k=1}^{\infty} c_k (\varepsilon_1 - \varepsilon_2)^k \qquad (2)$$

in which the coefficients of the expansion are:

$$c_k = \frac{(-1)^{k+1}}{k!} \left( \frac{d^k \varepsilon}{d\varepsilon_1^k} \right)_{\varepsilon_2}. \qquad (3)$$

Equation (2) reiterates that $\in = \in_2$ for $\in_1 = \in_2$. However, in practice it is necessary that the coefficients $c_k$ differ significantly from zero in order that experimental permittivity mismatch measurements, i.e. $\in_2 > \in_1$ or $\in_2 < \in_1$, enable the permittivity match case of Eq. (1) to be identified, as illustrated by way of example in the results shown in FIG. 1.

A large body of work exists for the formulation of mixture rules; i.e. the mixture permittivity function $\in(\in_1, \in_2, q_1, q_2)$ in terms of $\in_1$, $\in_2$, and the volume fractions $q_1$ and $q_2$ of the phases. The various approaches are effective medium approximations in which the grain length-scale is taken to be much smaller than the wavelength of an alternating electric field that is applied to the saturated rock/powder to measure permittivity. In an aspect of the present invention, these rules enable an approximate $c_k$ to be obtained to validate the experimental permittivity mismatch measurement method. The mixing rules fall broadly into two classes: those with an approximate theoretical basis and those that are empirical.

In the former class, the rules may be written as:

$$q_2 = \frac{(\varepsilon - \varepsilon_1)[\varepsilon_2 + 2\varepsilon_1 + v(\varepsilon - \varepsilon_1)]}{(\varepsilon_2 - \varepsilon_1)[\varepsilon + 2\varepsilon_1 + v(\varepsilon - \varepsilon_1)]} \quad (4)$$

where v=0, 1, 2, or 3 according to the particular internal electric field assumed in the formulation. For v=0 the Maxwell Garnett rule is found.

In the latter class, rules such as $$q_2 = \frac{(\varepsilon^n - \varepsilon_1^n)}{(\varepsilon_2^n - \varepsilon_1^n)}, \quad (5)$$

have been proposed, which for n=½ is the Complex Refractive Index Rule, and for n=⅓ is the rule attributed to Looyenga.

In the latter class there is also the logarithmic rule of Lichtenecker;

$$q_2 = \frac{\log(\varepsilon/\varepsilon_1)}{\log(\varepsilon_2/\varepsilon_1)}. \quad (6)$$

Relevant to embodiments of the present invention described herein is that for the rules discussed above, and for other mixing rules, the terms $c_1$ and $c_2$ are rule-independent and are given as follows:

$$c_1 = q_1, \quad (7)$$

and $$c_2 = -q_1 q_2/(N\in_2), \quad (8)$$

where:
N=3 for the relation of Equation (4) and
N=4 for the relations of Equations (5) and (6).

Thus from Equation (2), when the dielectric permittivity $\in$ is sufficiently close to the exact match condition ($\in_1 \cong \in_2$), $\in$ can be written as:

$$\varepsilon = \varepsilon_2 + q_1(\varepsilon_1 - \varepsilon_2) - \frac{q_1 q_2}{N\varepsilon_2}(\varepsilon_1 - \varepsilon_2)^2 + \ldots . \quad (9)$$

Equation (9) shows that as $\in_1 \cong \in_2$, the terms in $(\in_1 - \in_2)^k$ become negligibly small for k>2, and, hence, close to the match condition $\in_1 \cong \in_2$, $\in_1 = \in_2$, the relation is linear in form and can be written as:

$$\in = \in_2 + q_1(\in_1 - \in_2) \quad (10)$$

In an embodiment of the present invention, this linear form of relationship between the permittivity of the rock matrix and the matching liquid may be used to determine $\in_2$, the rock matrix permittivity. In such embodiments of the present invention, since the relationship is linear, only two data points from two permittivity measurements are required to determine $\in_2$. In aspects of the present invention, more than two measurements of permittivity of the saturated rock/powder may be measured to provide for enhanced accuracy of the calculated rock matrix permittivity.

In an embodiment of the present invention, a method for determining rock matrix permittivity is provided in which:
a) Mineral grains of a rock or a powder are put intimately in contact with an inert fluid of controlled permittivity;
b) Measurements are made of the inert fluid permittivity ($\in_1$) and of the combined permittivity of the rock or powder ($\in$) in contact with the inert fluid;
c) The matching liquid permittivity $\in_1$ is varied and the combined permittivity $\in$ of the rock or powder in contact with the inert fluid is measured.
d) A value of the matching liquid permittivity $\in_1$ is found that equals the combined permittivity $\in$ of the rock or powder in contact with the inert fluid. The permittivity $\in_2$ of the mineral grains of the rock or powder are then identical to the matching liquid permittivity $\in_1$.

In one embodiment of the above method, the steps (a) to (d) may be performed so that a partial separation of the rock or powder grains from the fluid is provided. In this arrangement, some of the rock/powder is in intimate contact with/is saturated by the liquid and a portion of the liquid is sufficiently removed from the rock/powder to allow its independent permittivity to be measured.

As noted previously, in a permittivity matching method/system, a fluid composition-variation method may be used to vary the matching liquid permittivity $\in_1$ by varying the fluid composition, by typically using a mixture of two or more non-reactive liquids. In practice, such methods may be, among other things, inconvenient and time-consuming as it is necessary to repeatedly saturate a core sample or powder of the rock and then measure the permittivity of the saturated sample sample/powder. Moreover, it is difficult to ensure the new liquid completely replaces the liquid that was previously saturating the rock sample/powder. Furthermore, such fluid composition variation methods cannot be used remotely or carried out automatically.

Figure 2:
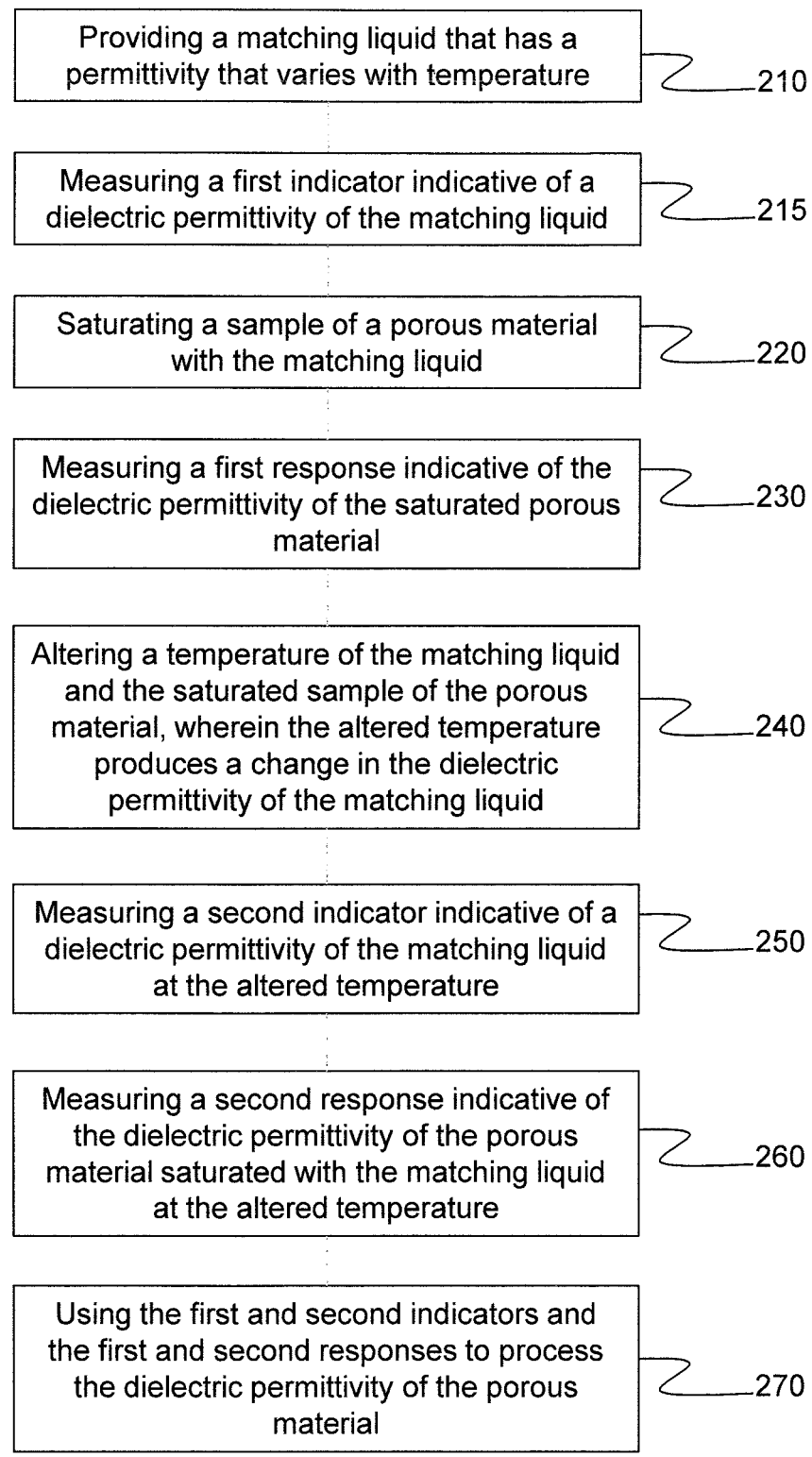
FIG. 2 illustrates a flow type diagram for a method of measuring a matrix permittivity of a porous material, in accordance with an embodiment of the present invention.

FIG. 2 illustrates a flow type diagram for a method of measuring a matrix permittivity of a porous material, in accordance with an embodiment of the present invention. In step 210 of the method, a matching liquid having a permittivity that varies with temperature is provided. The matching liquid may comprise a single liquid or a mixture of different liquids where the single liquid or the mixture of liquids has a permittivity that changes with a change in a thermodynamic property. Merely by way of example, the matching liquid may comprise hexanol, a liquid that has a permittivity that varies with temperature.

In step 215, a first indicator indicative of a dielectric permittivity of the matching liquid is measured. In some aspects of the present invention, the matching liquid may have a known permittivity so that the measuring of the first indicator indicative of a first dielectric permittivity of the matching liquid may comprise determining a permittivity of the fluid mixture for the existing thermodynamic properties. For example, the permittivity of the matching liquid at the existing thermodynamic properties may be found in a look up table, determined from previous experiments, processed from a model of the behaviour of the matching liquid and/or the like.

In other aspects of the present invention, a permittivity device may be used to measure a response of the matching liquid that is indicative of the permittivity of the matching liquid. Merely by way of example, an electrode, probe, dielectric electrode/probe and/or the like may be used to measure a capacitance, an impedance and/or the like of the matching liquid. The capacitance, impedance or the like of the matching liquid is indicative of the permittivity of the matching liquid. In other embodiments, a resonance measurement may be made where the resonant frequency associated with the matching liquid is indicative of the permittivity of the matching liquid and/or the saturated sample. In some embodiments a processor may be used to process the permittivity of the matching liquid from the measured capacitance, impedance, resonance and/or the like.

In step 220, a sample of the porous material (a rock sample, which may be a core, powder or the like) is saturated with the matching liquid. In some aspects of the present invention, the sample of the porous material may comprise a core or sample taken from the porous material. For example, the sample of the porous material may comprise a core removed from a subterranean formation. In aspects where the sample comprises a piece or a core of the porous material the fluid may be contacted with the matching liquid to provide for saturation of the sample. A pressure or the like may be applied to provide for saturation of the sample. In other aspects of the present invention, the sample of the porous material may comprise a powder or the like formed from the porous material. In such aspects, the powder may be suspended in the matching liquid.

In step 230, a first response indicative of the dielectric permittivity of the saturated porous material is measured. In some embodiments of the present invention, a permittivity device such as an electrode, probe, dielectric probe or the like may be used to measure a capacitance, impedance and/or the like of the saturated sample of the porous material. In other embodiments a resonant frequency of the saturated porous material may be determined. The conductance, impedance, resonant frequency and/or the like is indicative of the permittivity of the saturated sample. In some aspects of the present invention, the actual permittivity of the saturated sample may be processed from the indicative measurement.

In step 240, a temperature of the matching liquid and the saturated sample of the porous material is altered, wherein the altered temperature produces a change in the dielectric permittivity of the matching liquid. In an embodiment of the present invention, because the matching liquid is selected so that its permittivity varies with temperature, the result of changing the temperature is that the permittivity of the matching liquid is changed.

In some aspects of the present invention, a single device such as a heater, cooler and/or the like is used to change the temperature of both the matching liquid and the saturated sample. For example, the sample of the porous material may be contacted with and saturated by a reservoir of the matching liquid and reservoir may comprise a separate portion of the matching liquid that may be positioned away from, out of contact with and separate from the sample of the porous material. In such an example, a heater, cooler and or the like may control the temperature of both the reservoir and the saturated sample. In other aspects of the present invention, the matching liquid and the saturated sample may be contained separately from one another and one or more devices may be used to control the temperatures of the fluid mixture and the matching liquid.

In step 250 a second indicator indicative of a second dielectric permittivity of the matching liquid at the altered temperature is measured. In some aspects of the present invention, an electrode, probe, dielectric probe and/or the like may be used to measure a response such as a capacitance, an impedance and/or the like indicative of the permittivity of the matching liquid at the altered temperature. In other embodiments, a resonant frequency of the matching fluid may be determined, where the resonant frequency is indicative of the permittivity of the matching fluid. In some aspects, the measured indicator may be processed to determine the permittivity of the matching liquid at the changed temperature. In aspects of the present invention, where the saturated sample is contacted with a reservoir of the fluid mixture, the measurement of the indicator is made on the separate portion of the reservoir as defined above.

In step 260, a second response indicative of the dielectric permittivity of the porous material saturated with the matching liquid at the altered temperature is measured. In aspects of the present invention, the saturated sample has been heated, cooled or the like to the altered temperature and an electrode, probe and/or the like is used to measure a response, such as a capacitance, impedance and/or the like of the saturated sample that is indicative of the permittivity of the saturated sample. In other embodiments, a resonant frequency of the saturated porous sample may be determined, where the resonant frequency is indicative of the permittivity of the porous sample. In some aspects, the response is processed to determine the actual permittivity of the saturated sample at the altered temperature.

In step 270, a processor—which may comprise a computer, software for running on a computer and/or the like—may process a dielectric permittivity of the porous material from: (a) the first indicator indicative of the dielectric permittivity of the matching liquid; (b) the first response indicative of the dielectric permittivity of the saturated porous material; (c) the second indicator indicative of the dielectric permittivity of the matching liquid at the altered temperature; and (d) the second response indicative of the dielectric permittivity of the porous material saturated with the matching liquid at the altered temperature. In certain aspects where the measured indicators have been processed into actual permittivities of the fluid mixture and the saturated sample these may be used to process the dielectric permittivity of the porous material.

In certain aspects of the present invention, one or more additional temperature changes may be made to matching liquid and the saturated rock sample and responses indicative of the permittivity of the matching liquid and the saturated sample may be measured and used in the processing of the dielectric permittivity of the porous material. In such aspects, these additional measurements may increase the accuracy of the calculation of the dielectric permittivity of the porous material. In some embodiments of the present invention, differences between the permittivity of the saturated sample and the permittivity of the matching liquid at different temperatures may be used to process a value when the permittivity of the saturated sample is equal to that of the fluid mixture and this value will correspond to the permittivity of the rock matrix of the sample.

Figure 3:
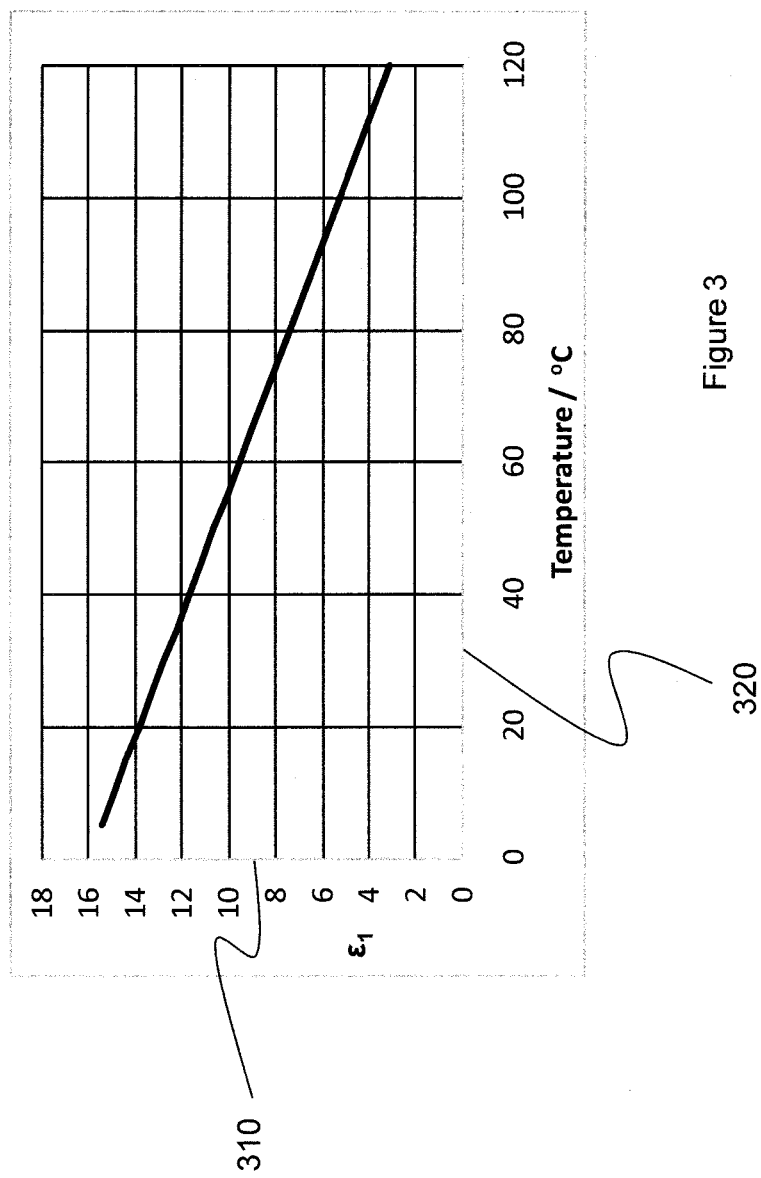
FIG. 3 illustrates how permittivity of a matching liquid, in this example hexanol, varies with temperature at atmospheric pressure, where the matching fluid is an example of a matching liquid for use in an embodiment of the present invention for determining rock matrix permittivity.

FIG. 3 illustrates how permittivity of a matching liquid, in this example hexanol, varies with temperature at atmospheric pressure, where the matching liquid is an example of a matching liquid for use in an embodiment of the present invention for determining rock matrix permittivity. As depicted in FIG. 3, a fluid permittivity $\in_1$ 310 is plotted against a temperature (° C.) 320. In accordance with an embodiment of the present invention, the fluid permittivity $\in_1$ is varied by varying the temperature. In other aspects of the present invention, other thermodynamic properties of the fluid, such as pressure, chemical composition and/or the like may be varied to cause a change in the permittivity of the fluid.

For solid minerals the variation with temperature, T, of the permittivity $\in(T)$, arises largely from the temperature dependence of the mineral density, $\rho(T)$, which is generally both known and small. A commonly-used connection between $\in(T)$ and $\rho(T)$ is given by the Clausius-Mossoti relation which states that $$(\in -1)/(\in +2)=K\rho \qquad (11)$$

where K is a constant for a given mineral.
Differentiation gives the permittivity temperature coefficient:

$$d\in/dT=-(\in-1)(\in+2)\gamma/3 \qquad (12)$$

where $\gamma$ is the mineral volume expansivity $(-d\rho/dT)/\rho$ which for a given matrix mineral is generally a well-known quantity and is temperature-independent. Thus, if $T_0$ is the temperature at match between the fluid and the saturated sample and the permittivity $\in(T)$ is required at another temperature T, then to a good approximation $$\in(T)=\in(T_0)+(d\in/dT)(T-T_0). \qquad (13)$$

The relationship between the permittivity of the rock sample and the temperature, for example as provided in Equation 13, may be accounted for in an embodiment of the present invention in the processing of the rock matrix permittivity. For example, in step 270 of FIG. 2, the processor may account for changes in the rock matrix permittivity for the different temperatures applied to the saturated rock sample as part of processing the rock matrix permittivity.

In embodiments of the present invention, signals indicative of the dielectric parameter of permittivity are measured. In aspects of the present invention, up to frequencies of approximately 50 MHz—hereinafter referred to as low frequency ("LF"), the permittivity may be measured using a pair of conductive electrodes disposed so as to subject the dielectric material to be interrogated—the fluid and the sample of the rock saturated in the fluid—to an electric field and the capacitance of the material may be measured using an impedance analyzer. Above about 100 MHz—hereinafter referred to as very high frequency ("VHF"), embodiments of the present invention may use measurements of the reflectance or transmittance of an electromagnetic wave as indicative of the permittivity of the material to be interrogated—the fluid and the sample of the rock saturated in the fluid.

Figure 4A:
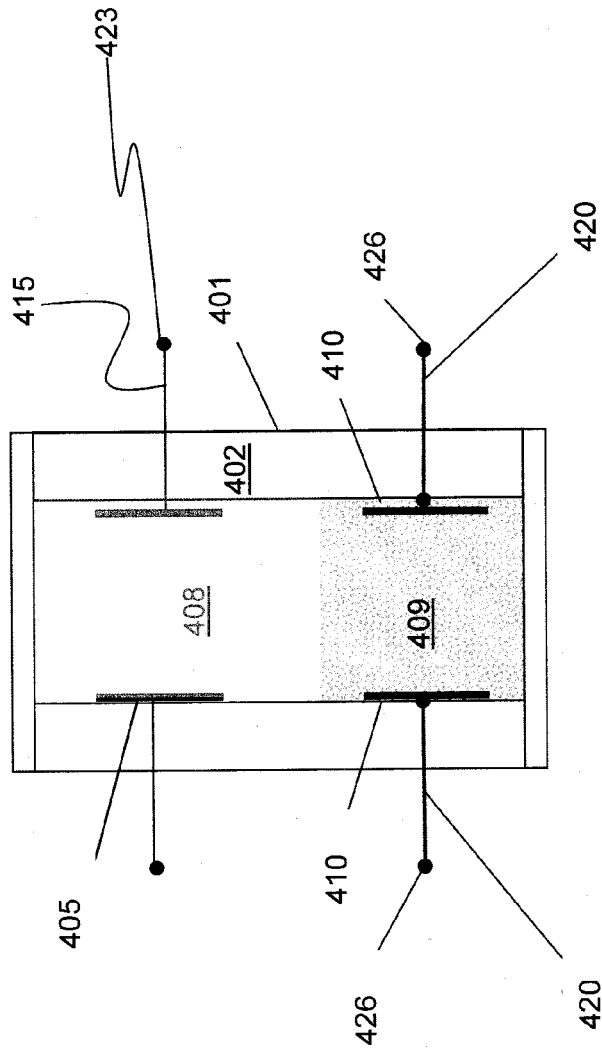
FIGS. 4A and 4B illustrate a system using low frequency interrogation for determining a rock matrix permittivity of a powdered rock sample, in accordance with an embodiment of the present invention.
Figure 4B:
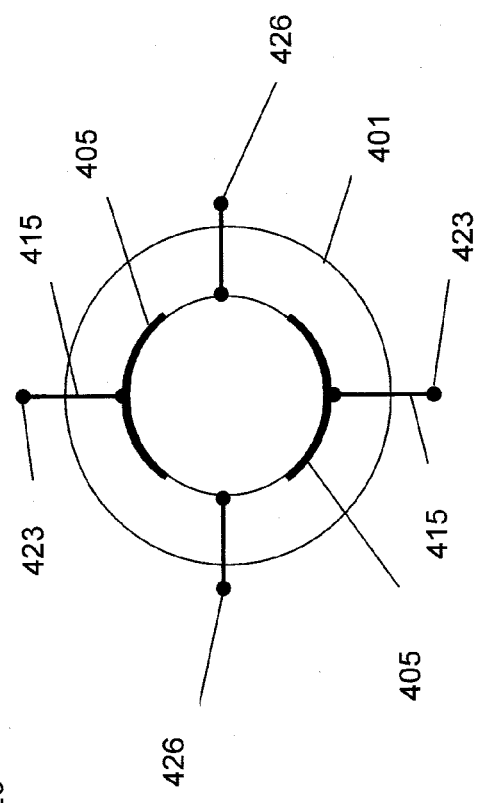

FIGS. 4A and 4B illustrate a system using low frequency interrogation for determining a rock matrix permittivity of a powdered rock sample, in accordance with an embodiment of the present invention. The system according to an embodiment of the present invention comprises a grounded conducting vessel 401. The vessel 401 comprises an insulating material 402. Inside the vessel 401 is a matching fluid 408 and a porous sample 409 that is saturated by the matching fluid 408. In certain aspects, the porous sample 409 comprises a powder sample that is mixed with the matching fluid 408 and allowed to sediment out from the matching fluid 408. In other aspects, the porous sample 409 comprises a sample of the porous material that may be disposed at the bottom of the vessel 401 and immersed in the matching fluid 408. In FIG. 4A, two regions may be created in the vessel 401, one region comprising the matching fluid 408 and one region comprising the porous sample 409 saturated by the matching fluid 408. In other embodiments (not shown), the matching fluid 408 may be placed in a reservoir 407 that may be interrogated separately from the porous sample 409.

In certain aspects, the vessel 401 is cylindrical. Two sets of electrode-pairs 405 and 410 are located along the vertical axis of the vessel 401. As depicted in FIG. 4A the two pairs of electrodes are disposed directly above one another whereas in FIG. 4b the connections are depicted for the two pairs of electrodes to be rotated through ninety degree (90°) with respect to one another. Contact to the electrode-pairs is made via connecting leads 415 and 420 to external terminals 423 and 426. The terminals 423 and 426 are in turn connected, either manually or automatically, to a permittivity indicative device not shown, which may comprise an impedance analyzer or the like, which measures the capacitances $C_A$ and $C_B$ of each electrode pair, where A and B denote the upper and lower pairs of electrodes, respectively. Each electrode occupies approximately a quadrant of the cylindrical vessel so that the electric field generated within a suspension from the potential applied by the network analyzer approximately samples the cross-section of the cylinder. In an embodiment of the present invention, the electrode-pairs. As shown in FIG. 4B, are disposed orthogonally around the vertical axis of the vessel 401 to minimize any capacitive interaction between the pairs of electrodes.

In general the measured capacitances $C_A$ and $C_B$ of each electrode pair are given by $$C_A = k_A \in_A,$$

$$C_B = k_B \in_B \qquad (15)$$

where $\in_A$ or $\in_B$ is the permittivity of the suspension or liquid in the spaces between the electrodes. The terms $k_A$ and $k_B$ are constants for a given electrode-pair configuration, which may be obtained by calibration using a liquid of known and stable permittivity, by solving numerically the Laplace equation for the electrode geometry and/or the like. In some aspects of the present invention, an assumption that $k_A=k_B$. may be used in the step of processing the permittivity of the rock matrix.

Several methods may be used with the system according to an embodiment of the present invention to determine the matrix permittivity of the porous sample 409.

In a first aspect of the present invention, the liquid permittivity $\in_1$ of the matching fluid 408 is varied by varying its thermodynamic properties until the permittivity of the porous sample saturated by the matching fluid $\in$ matches the liquid permittivity $\in_1$. When this occurs, the rock matrix permittivity $\in_2$ is as follows:

$$\in=\in_1=\in_2=\in_A=\in_B, \text{ and } C_A=C_B.$$

Thus varying the liquid permittivity $\in_1$ until $C_A=C_B$ gives the permittivity $\in_2$ of the porous sample when $\in=\in_1$.

In a second aspect, one electrode pair of the device of FIG. 4 may be removed. The liquid permittivity $\in_1$ is then varied, either by altering the temperature of the porous sample saturated by the matching fluid until the capacitance of the single electrode-pair is unaltered by any means of altering the volume fractions of the liquid and the porous sample in the inter-electrode space, e.g. by alternating the vessel's vertical orientation so that different volume fractions of the matching liquid and the porous sample are disposed between the electrodes. When this un-altering capacitance is found, the liquid and saturated porous sample permittivities are matched. The advantage of this method is that connections between the electrodes and the impedance analyzer can remain unbroken.

In a yet further aspect, a method which does not require a perfect match of $\in_2$ and $\in_1$ is provided in which the liquid permittivity $\in_1$ is varied above and below that of the saturated porous sample by altering the temperature of the matching liquid 408. At the same time $C_A$ and $C_B$ are measured for either the case where the matching liquid 408 is well mixed with porous sample or the porous sample 409 is sedimented out at the bottom of the vessel 401. In the sedimented case, the capacitance $C_A$ of the upper electrode pair gives $\in_1=\in_A=C_A/k_A$. In the well-mixed case, $\in_A=\in_B=\in$, and a plot of $\in$ versus $\in_1$ gives $\in_2$, as shown by Eq. (10) and FIG. 1. In the sedimented case, $C_B$ of the lower electrode pair gives $\in=\in_B=C_B/k_B$, and a plot of $\in$ versus $\in_1$ gives $\in_2$, as shown by Eq. (10)

and FIG. 1. The difference between these cases is that in the well-mixed case the liquid volume fraction $q_1$ is greater than $q_1$ for the sedimented bed.

FIGS. 5A and 5B illustrate a system using high frequency interrogation for determining a rock matrix permittivity of a powdered rock sample, in accordance with an embodiment of the present invention The methods of operation of the VHF system are the same as for the LF embodiments described above, but with the electrode-pairs of FIGS. 4A and 4B replaced by VHF reflection probes 502 and 503

In an embodiment of the present invention, the dielectric permittivity is assumed to be proportional to the capacitance measured by measured/indicated by the VHF reflection probes 502 and 503. In the figure a vessel 501 contains a powdered sample of the porous material that is saturated with a matching fluid. As depicted, the powdered sample of the porous material has formed a saturated porous sample layer 509 with a matching liquid layer 508 deposited above.

In aspects of the present invention, the VHF reflection probes 502 and 503 consist of a central electrode 504 insulated electrically from an outer cylindrical electrode 505 by a solid insulating material 506. In an embodiment of the present invention, an electric field established between the central electrode 504 and the outer cylindrical electrode 505 is used to sense permittivity. Accordingly, the probe is placed in contact with or appurtenant to the matching liquid and the saturated rock sample in order to take measurement of or indicative of the permittivity of the matching liquid and the saturated rock sample. As previously described, the permittivity of the matching liquid and/or the saturated rock sample may be varied by varying the applied temperature.

Figure 6:
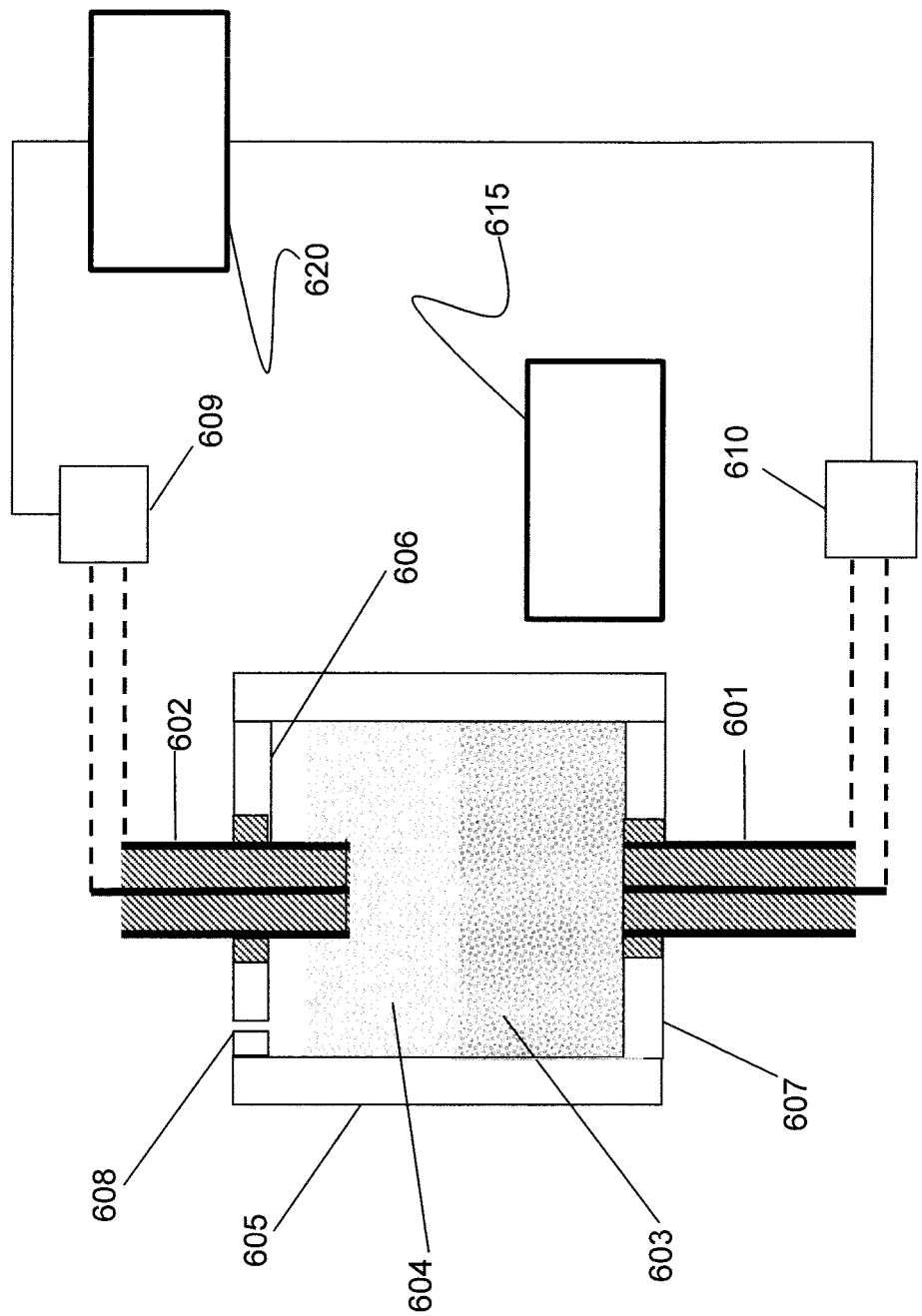
FIG. 6 depicts a system for measuring a permittivity of a rock sample in accordance with an embodiment of the present invention.

FIG. 6 depicts a system for measuring a permittivity of a rock sample in accordance with an embodiment of the present invention. The depicted system may be configured for use with LF or VHF probes for obtaining signals indicative of permittivity of the liquids and the sample saturated in the liquid.

In FIG. 6 a variable permittivity liquid 604 is disposed in a container 605. In an embodiment of the present invention, a matching liquid 604 may comprise a liquid or mixture of liquids with a permittivity that may vary according to the thermodynamic properties of the matching liquid 604, i.e., the temperature of the matching liquid 604. In an embodiment of the present invention, a sample mixture 603 comprises a sample of the porous rock that is saturated with the matching liquid 604. In some embodiments of the present invention, the sample mixture 603 may comprise a core of a rock formation, a powder of a rock sample or the like saturated by or suspended in the matching liquid 604. In some aspects of the present invention, the matching liquid 604 may be in fluid communication with the sample mixture 603. In other aspects of the present invention, a separator (not shown) may be used to separate the matching liquid 604 and the sample mixture 603.

In certain aspects of the present invention, the rock core, rock sample or powdered sample, hereinafter referred to as the core is completely saturated with the matching liquid 604, without residual air or gas bubbles. In an embodiment of the present invention, a mixture probe 601 may be used to sense a response of the sample mixture 603 indicative of the permittivity $\in_1$ of the sample mixture 603. In some aspects of the present invention, the mixture probe 601 may comprise two or more electrodes for measuring a capacitance, impedance or the like of the sample mixture 603. In other aspects of the present invention, the mixture probe 601 may comprise VHF reflection/transmittance probes or the like for measuring transmittance and/or reflection of an electromagnetic wave through a portion of the sample mixture 603, where the amount of the transmittance and or reflection of the electromagnetic wave is indicative of the permittivity of the sample mixture 603.

In an embodiment of the present invention, a liquid probe 602 may be used to sense a response of the matching liquid 604 that is indicative of the permittivity $\in_2$ of the matching liquid 604. In some aspects of the present invention, the liquid probe 602 may comprise electrodes for measuring a capacitance, impedance or the like of the liquid probe 602. The electrodes may be disposed apart from one another and separated by a portion of the matching liquid 604 that is separated from and not in contact with the sample mixture 603. In other aspects of the present invention, the liquid probe 602 may comprise one or more VHF reflection/transmittance probes or the like for measuring transmittance and or reflection of an electromagnetic wave through a portion of the sample mixture 603, where the amount of the transmittance and or reflection of the electromagnetic wave is indicative of the permittivity of the matching liquid 604.

In some embodiments, the mixture probe 601, the liquid probe 602, the sample mixture 603 and the matching liquid 604 may be disposed in a cell 605. In certain aspects, the cell 605 may be cylindrical and may comprise an upper end-cap 606 and a lower end-cap 607. In some embodiments of the present invention, a hole 608 in the cell 605 may allow for expansion of the matching liquid 604 liquid and/or vapor produced by the matching liquid 604.

In an embodiment of the present invention, a temperature controller 615 may be used to control the temperature of the cell 605. The temperature controller 615 may comprise a heater, a cooler and/or the like. Merely by way of example, the temperature controller 615 may control the temperature of the cell 605 to within about ±0.1 deg C. In aspects of the present invention, the cell 605 may comprise an insulating material to provide for temperature equivalence between the sample mixture 603 and the matching liquid 604.

In one embodiment of the present invention, the mixture probe 601 and/or the liquid probe 602 may comprise a dielectric probe(s) and may measure a capacitance, impedance or the like of the sample mixture 603 and/or the matching liquid 604. In aspects of the present invention a liquid probe controller 609 and a mixture probe controller 610 may control the liquid probe 602 and the mixture probe 601, respectively. The liquid probe controller 609 and the mixture probed controller 610 may comprise or be coupled with a processor, software and/or the like to provide for controlling the liquid probe 602 and/or the mixture probe 601. The liquid probe controller 609 and the mixture probed controller 610 may be in communication with a processor 620, which may receive responses indicative of the permittivity of the sample mixture 603 and the matching liquid 604 and may process a rock matrix permittivity for the rock core/powder in the sample mixture 603 from the indicative responses.

In some embodiments of the present invention, the mixture probe 601 and the liquid probe 602 are identical, i.e. the mixture probe 601 and the liquid probe 602 are configured to read the same permittivity under the same dielectric and temperature conditions. In aspects, where the mixture probe 601 and the liquid probe 602 are not identical, a mutual calibration may be made in which the signals from each of the mixture probe 601 and the liquid probe 602 are logged under the same dielectric and temperature conditions, e.g. with both probes sensing only the liquid during a temperature sweep. In an embodiment of the present invention, a temperature is found at which $\in_1 = \in_2$ and this permittivity value is the permittivity of the rock matrix of the core/power/sample of the rock in the sample mixture 603.

Figure 7:
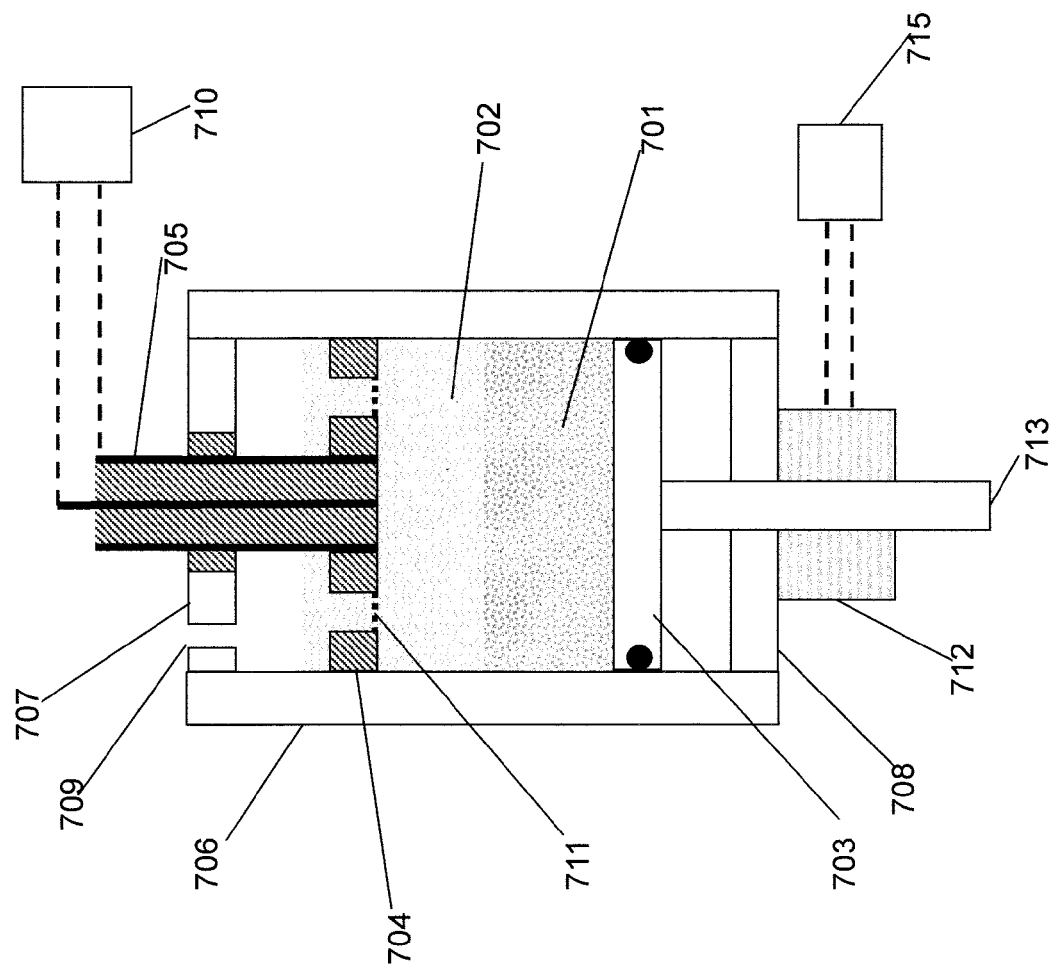
FIG. 7 illustrates an automated method for rock matrix permittivity measurement, in accordance with an embodiment of the present invention.

FIG. 7 illustrates an automated method for rock matrix permittivity measurement, in accordance with an embodiment of the present invention. In one automated embodiment, a single probe 705 may be used. In such aspects, signals from the single probe 705 may be logged automatically as the temperature and permittivity of a matching liquid 702 is swept with time. In some embodiments, only a single dielectric probe, the single probe 705, is used in place of the separate mixture probe and liquid probe. The single probe 705 may be to alternately measures the permittivity of the matching liquid 702 and the sample mixture 701. The advantage of using one probe is that it removes the need for mutual calibration of two probes, as described in the automated two-probe method, above.

In an embodiment of the present invention, a temperature sweep rate is performed slowly enough to ensure temperature equilibration throughout a cell 706 containing the matching liquid 702 and the sample mixture 701. In certain aspects of the present invention it is assumed that the rock sample in the sample mixture 701 is completely saturated with the matching liquid 702, without residual air bubbles.

In some embodiments of the present invention, the cell 706 includes a piston 703, and a registration plate 704. The registration plate 704 allows the piston 703 to push the rock sample in the sample mixture 701 into contact with the single probe 705. The registration plate 704 allows the matching liquid 702 to pass through the matching liquid 702 via holes 711 in the matching liquid 702. The holes 711 may be covered with a grid of suitable mesh to contain the core material the core material is in powder form.

In aspects of the present invention, when the piston 703 is near a bottom plug 708 of the cell 706, the single probe 705 measures the permittivity of the matching liquid 702. When the piston 703 is pushed upward by the action of a motor 712 on a rod 713, initiated by a motor control 715, the rock sample, rock core and/or rock powder in the sample mixture 701 is pushed into contact with the single probe 705. When this contact occurs, single probe 705 measures a signal that is indicative of the permittivity of the sample mixture 701. The process of moving the sample mixture 701 into and out of contact with the single probe 705 may be repeated as the temperature is raised. At some point during a temperature sweep, a temperature from a temperature controller (not shown) or a temperature measuring device (not shown) in contact with the sample mixture 701 and/or the matching liquid 702 in the cell is measured at which the single probe 705 outputs a signal indicative of permittivity that is the same whether the piston 703 is raised or lowered. This signal can be used to process the rock matrix permittivity.

In certain aspects of the present invention, permittivity matching measurements, as described above, may be performed downhole in a wellbore. In some aspects, samples of formation rock may be sampled and tested downhole.

Figure 8A:
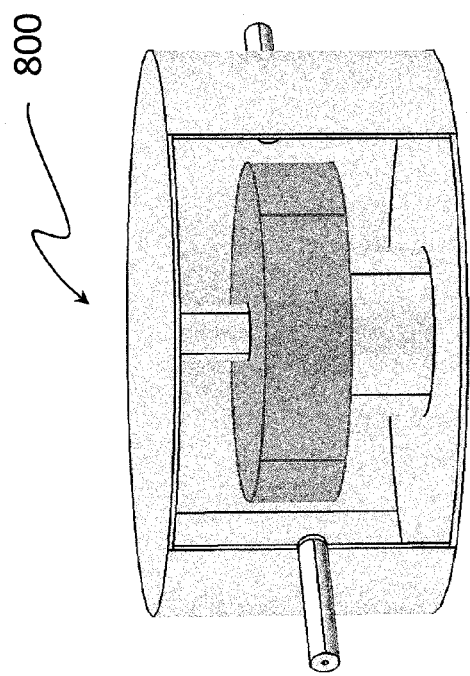
FIGS. 8A & 8B illustrate a resonator cavity system for rock matrix permittivity measurement, in accordance with an embodiment of the present invention.
Figure 8B:
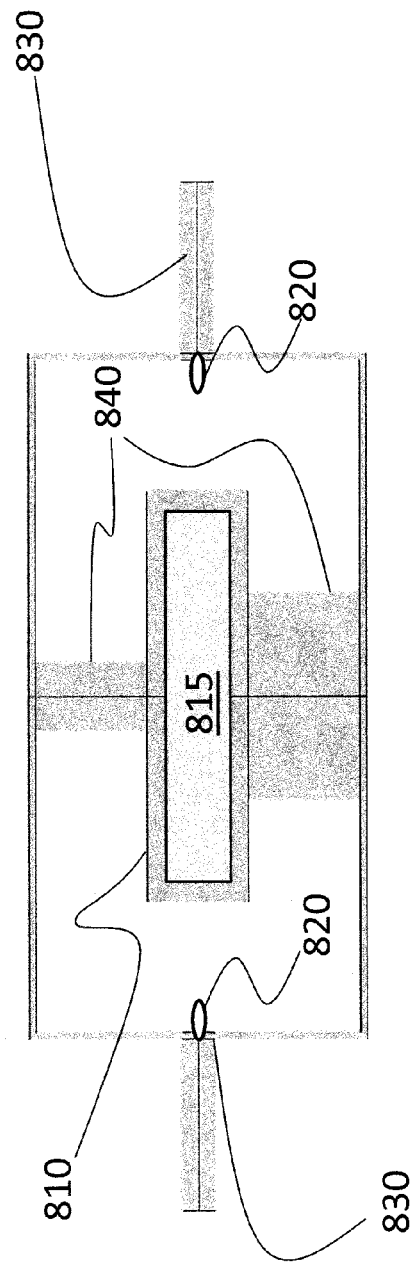

FIGS. 8A and 8B illustrate a resonance apparatus for measuring a rock matrix permittivity in accordance with an embodiment of the present invention. Various resonator, cavity and re-entrant cavity arrangements may be used as measurement geometries for dielectric permittivity. These systems create an electromagnetic resonant structure which when excited has a resonant frequency dependent on the permittivity of the dielectric material within. Further the loss tangent may be determined from the Q factor of the resonance. In general, this class of device is much more accurate than the corresponding reflection or waveguide systems for low loss materials, but can only measure at the resonant frequency and at higher order modes. For mineral systems, which are intrinsically low loss systems, a resonant method may be used to obtain accurate indicators of permittivity of the fluid and fluid mixtures within the resonator.

FIG. 8A illustrates a $TE_{01\delta}$ cavity for making resonance-type measurements of a dielectric sample in accordance with an embodiment of the present invention. The illustrated cavity design is merely an example of one of many designs that may be used in embodiments of the present invention.

FIG. 8B illustrates a cross-sectional view of the resonator cavity of FIG. 8A. In the illustrated cavity 800, a dielectric sample container 810 is used to hold a dielectric sample 815. In certain embodiments of the present invention, a matching liquid (not shown) is disposed in the dielectric sample container 810 along with the dielectric sample 815. For example, the matching liquid may be mixed with a powdered sample of the dielectric sample 815. In other arrangements, the matching liquid may be saturating a non-powdered sample of the dielectric sample 815. The dielectric sample container 810 is supported in the cavity 800 by dielectric supports 840.

The resonator cavity 800 may comprise a plurality of transducers 820 for interrogating the dielectric sample 815. The transducers 820 may be coupled with a body of the cavity 800 by a plurality of couplings. The transducers may be used to determine resonance values for the dielectric sample 815 and/or the matching fluid. The methods and system described above may be used with the cavity 800 to determine a matrix permittivity of the dielectric sample 815 from resonance measurements made on the dielectric sample 815 saturated with the matching fluid.

A wide range of methods for measuring quantities sensitive to permittivity are known. Permittivity may be deduced from the quantity measured using one of these known methods by employing a theoretical model of the measuring device configuration for the method. The known methods fall broadly into three categories: (i) capacitive measurement, (ii) RF reflection or transmission coefficient measurement, and (iii) cavity resonance measurement. An example of a capacitance method is to measure the value of capacitance of a device, usually a circular parallel plate capacitor, with the material to be determined filling the space between the plates. An example of an RF reflection device is a coaxial-end-probe, with the material under test filling the half space at the end of the probe. The RF reflection coefficient (amplitude and phase) is sensitive to the material permittivity. Similarly, the material may be introduced to a well defined section of a coaxial transmission line and the transmission coefficient measured. Last, cavity resonators are particularly well suited to precise measurement of resonant frequency and resonance width (Q factor). A test material introduced to fill or partially fill, or interact with the cavity will affect both the resonant frequency and Q-factor from which the material permittivity, at the resonant frequency, can be determined. Any of the above methods, combinations of the above methods and/or other methods of measuring quantities sensitive to permittivity may be used in embodiments of the present invention.

While the principles of the disclosure have been described above in connection with specific apparatuses and methods, it is to be clearly understood that this description is made only by way of example and not as limitation on the scope of the invention.

What is claimed is:

1. A method for determining a matrix permittivity of a porous material, the method comprising:
   measuring a first indicator indicative of a first dielectric permittivity of a fluid composition;
   saturating the porous material with the fluid composition;

measuring a first response indicative of the dielectric permittivity of the saturated porous material;

altering a thermodynamic property of the fluid composition, wherein the altered thermodynamic property produces a change in the dielectric permittivity of the fluid composition;

measuring a second indicator indicative of a second dielectric permittivity of the altered fluid composition;

measuring a second response indicative of the dielectric permittivity of the porous material saturated with the thermodynamically altered fluid composition;

using the first and second indicators and the first and second responses to process the matrix permittivity of the porous material.

2. The method of claim 1, wherein the step of using the first and second dielectric permittivities and the first and second responses to process the matrix permittivity of the porous material comprises processing from the first and second dielectric permittivities and the first and second responses a value where a permittivity of the porous material is equal to the permittivity of the fluid composition.

3. The method of claim 2, wherein the matrix permittivity of the porous material is calculated from the value.

4. The method of claim 1, wherein the first dielectric permittivity is known.

5. The method of claim 1, wherein the first dielectric permittivity is measured.

6. The method of claim 1, wherein the first dielectric permittivity comprises a first measured value indicative of the first dielectric permittivity.

7. The method of claim 6, wherein the first measured value comprises at least one of a measured capacitance of the fluid composition, a measured reflectance of an electromagnetic wave from the fluid composition and a measured transmittance of an electromagnetic wave through the fluid composition.

8. The method of claim 1, wherein the second dielectric permittivity is determined using at least one of a look up table, experimental modeling, previous analysis of the fluid composition and theoretical modeling.

9. The method of claim 1, wherein the second dielectric permittivity is measured.

10. The method of claim 1, wherein the second dielectric permittivity comprises a second measured value indicative of the second dielectric permittivity.

11. The method of claim 10, wherein the second measured value comprises at least one of a measured capacitance of the altered fluid composition, a measured reflectance of an electromagnetic wave from the altered fluid composition, a measured transmittance of an electromagnetic wave through the altered fluid composition and a measured resonance behaviour of an electromagnetic resonator coupled to the altered fluid composition.

12. The method of claim 6, wherein the second dielectric permittivity comprises a second measured value indicative of the second dielectric permittivity.

13. The method of claim 1, wherein the first response comprises at least one of a measured capacitance of the saturated porous material, a measured reflectance of an electromagnetic wave from the saturated porous material, a measured transmittance of an electromagnetic wave through the saturated porous material.

14. The method of claim 1, wherein the porous material comprises at least one of a rock sample and a powdered sample of a mineral.

15. The method of claim 1, wherein the porous material comprises a portion of a subterranean formation.

16. The method of claim 1, wherein the step of altering the property of the fluid composition comprises heating the fluid composition.

17. The method of claim 1, wherein the step of altering the property of the fluid composition comprises heating the porous material saturated with the fluid composition.

18. The method of claim 1, wherein the step of altering the property of the fluid composition comprises adjusting a composition of the fluid composition.

19. The method of claim 1, wherein the step of measuring the second response indicative of the dielectric permittivity of the porous material saturated with the altered fluid composition comprises saturating a second sample of the porous material with the altered fluid composition and measuring the second response.

* * * * *